US010702300B2

(12) United States Patent
Higgins et al.

(10) Patent No.: US 10,702,300 B2
(45) Date of Patent: Jul. 7, 2020

(54) METHODS, DEVICES AND SYSTEMS FOR SLOW ROTATION OF DRIVE SHAFT DRIVEN ATHERECTOMY SYSTEMS

(71) Applicant: CARDIOVASCULAR SYSTEMS, INC., New Brighton, MN (US)

(72) Inventors: Joseph P. Higgins, Minnetonka, MN (US); Kraig A. Karasti, Brooklyn Park, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 0 days.

(21) Appl. No.: 14/801,333

(22) Filed: Jul. 16, 2015

(65) Prior Publication Data

US 2016/0015420 A1    Jan. 21, 2016

Related U.S. Application Data

(60) Provisional application No. 62/026,279, filed on Jul. 18, 2014.

(51) Int. Cl.
*A61B 17/3207* (2006.01)
*A61B 17/32* (2006.01)

(52) U.S. Cl.
CPC .. *A61B 17/320758* (2013.01); *A61B 17/3207* (2013.01); *A61B 2017/320004* (2013.01);
(Continued)

(58) Field of Classification Search
CPC ....... A61B 2017/320766; A61B 2017/320032; A61B 2017/320004; A61B 17/3207; A61B 17/320758; A61B 17/320708; A61B 17/320725; A61B 17/320783; A61B 17/320016; A61B 17/32002; A61B 17/32075; A61B 2017/320733;
(Continued)

(56) References Cited

U.S. PATENT DOCUMENTS 5,314,407 A    5/1994 Auth et al.
5,766,192 A *  6/1998 Zacca ............ A61B 17/320725
                                                    606/159
(Continued)

FOREIGN PATENT DOCUMENTS

CN    102056555       5/2011
CN    102056558 A     5/2011
(Continued)

OTHER PUBLICATIONS

International Preliminary Report on Patentability for PCT Application No. PCT/US2015/040844 dated Jul. 17, 2015, dated Feb. 2, 2017.
(Continued)

*Primary Examiner* — Katherine H Schwiker
(74) *Attorney, Agent, or Firm* — Barnes & Thornburg LLP; Jeffrey R. Stone

(57) ABSTRACT

The present system is directed in various embodiments to methods, devices and systems for rotational atherectomy procedures. More specifically, embodiments comprise a rotational driver with rotational drive shaft and abrasive element attached thereto, the rotational driver being controlled by the rotational controller to rotate at unsustained low rotational speeds and/or rotational direction.

14 Claims, 4 Drawing Sheets

(52) U.S. Cl.
CPC .............. *A61B 2017/320032* (2013.01); *A61B 2017/320766* (2013.01)

(58) Field of Classification Search
CPC ....... A61B 2017/320741; A61B 2017/320775; A61B 2017/320791; A61B 2017/320024; A61B 2017/320028; A61B 2017/00172; A61B 2017/00176; A61B 2017/00181; A61B 2017/00185; A61B 2017/0019; A61B 2017/00194
USPC ................................ 606/159, 170–171, 180
See application file for complete search history.

(56) References Cited

U.S. PATENT DOCUMENTS

| | | | |
|---|---|---|---|
| 9,101,387 B2 | 8/2015 | Plowe et al. | |
| 2010/0121361 A1 | 5/2010 | Plowe et al. | |
| 2010/0125276 A1 | 5/2010 | Palermo | |
| 2011/0004107 A1* | 1/2011 | Rosenthal | A61B 17/32075 600/479 |
| 2012/0046679 A1* | 2/2012 | Patel | A61B 1/00179 606/159 |
| 2012/0078279 A1* | 3/2012 | Mark | A61B 10/0275 606/171 |
| 2013/0018398 A1 | 1/2013 | Rivers et al. | |
| 2013/0023770 A1* | 1/2013 | Courtney | A61M 25/10 600/467 |
| 2013/0253552 A1* | 9/2013 | Schoenle | A61B 17/320758 606/159 |
| 2014/0222042 A1* | 8/2014 | Kessler | A61B 17/320758 606/159 |
| 2015/0094745 A1* | 4/2015 | Blackledge | A61B 17/320758 606/159 |
| 2015/0208922 A1* | 7/2015 | Simpson | A61B 17/320783 600/427 |
| 2015/0216553 A1* | 8/2015 | Kessler | A61B 17/320758 606/159 |

FOREIGN PATENT DOCUMENTS

| | | |
|---|---|---|
| WO | 2009/148805 | 12/2009 |
| WO | 2013/056262 A1 | 4/2013 |
| WO | 2014/074764 A1 | 5/2014 |

OTHER PUBLICATIONS

Extended European Search Report, dated Mar. 19, 2018, for European Patent Application No. 15821535.0 based on PCT Application No. PCT/US2015/040844, filed Jul. 17, 2015.

* cited by examiner

METHODS, DEVICES AND SYSTEMS FOR SLOW ROTATION OF DRIVE SHAFT DRIVEN ATHERECTOMY SYSTEMS

CROSS-REFERENCE TO RELATED APPLICATIONS

This application claims priority to App. Ser. No. 62/026,279, entitled "Slow Rotation for Driveshaft Driven System", filed Jul. 18, 2014, the entire contents of each of which are hereby incorporated by reference.

FIELD OF THE INVENTION

The present invention generally relates to methods, devices and systems for rotational atherectomy procedures.

DESCRIPTION OF THE RELATED ART

Atherectomy is a non-surgical procedure to open blocked coronary arteries or vein grafts by using a device on the end of a catheter to cut or shave away atherosclerotic plaque (a deposit of fat and other substances that accumulate in the lining of the artery wall). For the purposes of this application, the term "abrading" is used to describe the grinding and/or scraping action of such an atherectomy head.

Atherectomy is performed to restore the flow of oxygen-rich blood in arteries to improve blood flow to the heart, to relieve chest pain, and to prevent heart attacks. Atherectomy is also used in other vascular territories such as the leg to relieve claudication and critical leg ischemia. It may be done on patients with chest pain who have not responded to other medical therapy and on certain of those who are candidates for balloon angioplasty (a surgical procedure in which a balloon catheter is used to flatten plaque against an artery wall) or coronary artery bypass graft surgery. It is sometimes performed to remove plaque that has built up after a coronary artery bypass graft surgery.

Atherectomy uses a rotating shaver or other device placed on the distal end of a catheter to slice away or destroy plaque. At the beginning of the procedure, medications to control blood pressure, dilate the coronary arteries, and prevent blood clots are administered. The patient is awake but sedated. The catheter is inserted into an artery in the groin, leg, or arm, and threaded through the blood vessels into the blocked coronary artery. The cutting head is positioned against the plaque and activated, and the plaque is ground up or suctioned out.

The types of atherectomy are rotational, directional, and transluminal extraction. Rotational atherectomy uses a high speed rotating abrasive element to grind up plaque and is performed at a sustained high rotational speed. Directional atherectomy was the first type approved, but is no longer commonly used for vessels in the heart; it scrapes plaque into an opening in one side of the catheter. Transluminal extraction coronary atherectomy uses a device that cuts plaque off vessel walls and vacuums it into a bottle. It is used to clear bypass grafts.

Performed in a cardiac catheterization lab, atherectomy is also called removal of plaque from the coronary arteries. It can be used instead of, or along with, balloon angioplasty.

Several devices have been disclosed that perform rotational atherectomy. For instance, U.S. Pat. No. 5,360,432, issued on Nov. 1, 1994 to Leonid Shturman, and titled "Abrasive drive shaft device for directional rotational atherectomy" discloses an abrasive drive shaft atherectomy device for removing stenotic tissue from an artery, and is incorporated by reference herein in its entirety. The device includes a rotational atherectomy apparatus having a flexible, elongated drive shaft having a central lumen and a segment, near its distal end, coated with an abrasive material to define an abrasive segment. At sufficiently high rotational speeds, the abrasive segment expands radially, and can sweep out an abrading diameter that is larger than its rest diameter. In this manner, the atherectomy device may remove a blockage that is larger than the catheter itself. Use of an expandable head is an improvement over atherectomy devices that use non-expandable heads; such non-expandable devices typically require removal of particular blockages in stages, with each stage using a differently-sized head.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

A typical atherectomy device includes a single-use disposable portion, which can be attached and detached from a non-disposable control unit (also referred to as a controller). The disposable portion includes elements that are exposed to saline and to the bodily fluids of the patient, such as a handle, a catheter, a rotatable drive shaft, and an abrasive head. The handle includes a turbine that rotates the drive shaft, and a knob that can longitudinally advance and retract the drive shaft along the catheter. Often, the device has a foot switch that activates the handle.

Typical known atherectomy devices use pneumatic power to drive the drive shaft, with the controller managing the amount of compressed air that is delivered to the turbine in the handle. The compressed air spins the turbine that, in turn, spins the drive shaft, and spins an abrasive crown attached to the drive shaft. Orbiting motion of the crown enlarges and widens the channel opening of a restricted or blocked vascular vessel.

Generally, multiple filar-wound drive shafts used in high-speed Orbital Atherectomy Devices (OAD) may open or expand when loaded depending on the winding direction relative to the rotational direction of the drive shaft during operation. Such spin-to-open shafts expand under load, with the filar spacing being increased. Alternatively, or in addition, if spacing is not increased under load, the shaft length is reduced. In either case, the outer diameter of the drive shaft increases.

When the load is reduced or the shaft ceases high-speed rotation, the shaft may spring back to its static state. This spring-back action can catch or tear biological material, resulting in unintentional vessel damage and trauma as well as trapping material between the wire filars. In addition, the spring-back action can dampen the force actually transmitted and applied to the abrasive element or crown attached to the drive shaft at a distal end.

In contrast, spin-to-close drive shafts may have a similar but opposite effect to that discussed above with the spin-to-open shafts. Spin-to-close shafts may wrap tighter when loaded or during rotation and may capture unwanted material between the filars of the wire. In addition, the drive shaft length may be extended beyond its static length and the outer diameter may be reduced. If such a shaft is sufficiently loaded, its outer diameter may be reduced to the point that it locks onto the guide wire.

Known rotational atherectomy systems do not have unsustained rotational speed or rotational direction capabilities that are controlled by a controller. Instead, operators of known devices control the rotational speed and direction manually at the handle or with a foot pedal.

Moreover, the opening and closing, or loading and unloading of known drive shafts result in unwanted friction between sliding components during high-speed rotation.

Consequently, unmet needs still exist in the removal of lesions.

BRIEF SUMMARY OF THE INVENTION

The present system is directed in various embodiments to methods, devices and systems for rotational atherectomy procedures. More specifically, embodiments comprise a rotational driver with rotational drive shaft and abrasive element attached thereto, the rotational driver being controlled by the rotational controller to rotate at unsustained low rotational speeds and/or rotational direction.

DETAILED DESCRIPTION

Figure 1:
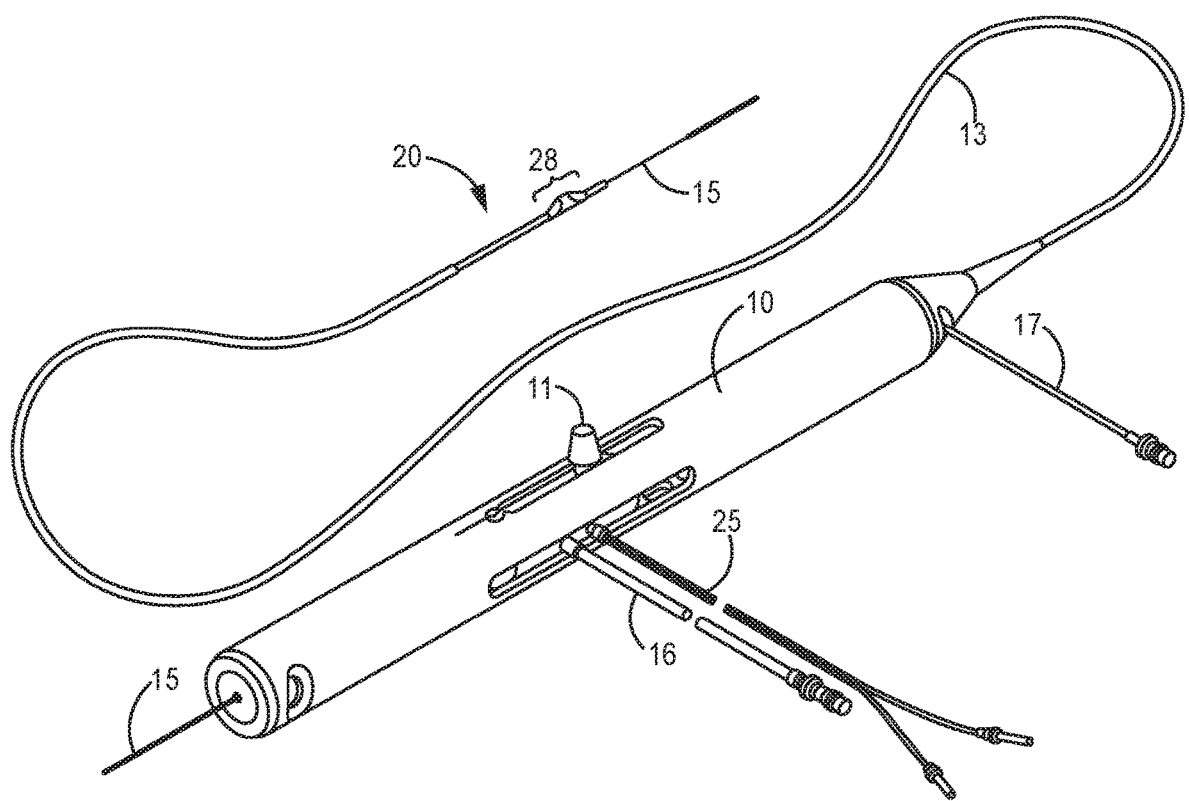
FIG. 1 illustrates one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

An atherectomy device is disclosed, with a motor or turbine with a maximum speed setting to ensure only slow rotation of a connected wire drive shaft that is capable of spinning-to-open and spinning-to-close, depending on the rotational direction of the motor or turbine. In this context, slow rotation comprises preferably less than 50,000 rpm, more preferably less than 25,000 rpm and still more preferably less than 5,000 rpm. Still more preferably, the slow rotation of the present invention comprises a non-sustained mode that is tunable to facilitate and improve tracking of the drive shaft as well as eliminate static friction between sliding components during loading and unloading.

The preceding paragraph is merely a summary, and should not be construed as limiting in any way. A more detailed description of the several embodiments follows.

FIG. 1 is a schematic drawing of a one embodiment of the present invention, a rotational atherectomy device. The device includes a handle portion 10, an elongated, flexible drive shaft 20 having an eccentric enlarged abrading head 28, and an elongated catheter 13 extending distally from the handle portion 10. The drive shaft 20 is constructed from helically coiled wire as is known in the art and the abrading head 28 is fixedly attached thereto. The catheter 13 has a lumen in which most of the length of the drive shaft 20 is disposed, except for the enlarged abrading head 28 and a short section distal to the enlarged abrading head 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20. Details regarding such handles and associated instrumentation are well known in the industry, and are described, e.g., in U.S. Pat. No. 5,314,407, issued to Auth, and incorporated by reference herein in its entirety. The handle 10 also desirably includes a control knob 11 for advancing and retracting the turbine and drive shaft 20 with respect to the catheter 13 and the body of the handle.

The abrasive element 28 in FIG. 1 is illustrated as an exemplary eccentric solid crown, attached to the drive shaft 20 near the distal end of the drive shaft 20. The term "eccentric" is used herein to denote that the center of mass of the crown is laterally displaced away from the rotational axis of the drive shaft 20. As the drive shaft rotates slowly, i.e., less than a maximum of 50,000 and preferably less than 5,000 rpm, the displaced center of mass of the crown causes the drive shaft to flex radially outward in the vicinity of the crown as it spins, so that the crown may abrade over a larger diameter than its own rest diameter. Eccentric solid crowns are disclosed in detail in, for example, U.S. patent application Ser. No. 11/761,128, filed on Jun. 11, 2007 to Thatcher et al. under the title, "Eccentric abrading head for high-speed rotational atherectomy devices", published on Dec. 11, 2008 as U.S. Patent Application Publication No. US2008/0306498, and incorporated by reference herein in its entirety. The present invention is not, however, limited to an eccentric abrading head or crown. As the skilled artisan will recognize, any abrading, grinding, cutting and/or ablating element attached to the drive shaft, or formed from the drive shaft, whether eccentric or concentric, is well within the scope of the present invention.

An electric motor may replace the turbine of FIG. 1 for purposes of the present invention. Such a motor has different mechanical characteristics than the turbine, such as an increased rotational inertia. In addition to the motor, many or all of the other elements of the known atherectomy device of FIG. 1 may be used with the present disclosed head design, including the catheter 13, the guide wire 15, the control knob 11 on the handle 10, the helically coiled drive shaft 20 and the eccentric solid crown 28.

The rotational driver, e.g., motor or turbine, may comprise a maximum speed that is considered within the low rotational limit of the present invention. For example, an electric motor may comprise a closed loop speed control that ensures the maximum low rotational speed limit is not exceeded.

In addition, or alternatively, control electronics may be employed that may be set to a low rotational speed as defined herein.

The speed and rotational direction of the rotational driver, e.g., electric motor or turbine, may be controlled with a motor control integrated circuit triggered by logic signals from an integrated microprocessor or the like. Alternatively, pulse width modulation (PWM) signals may be used by the microprocessor to control the driver's speed and rotational direction. In an embodiment using PWM, the pulse width (voltage) controls the speed and the order in which the signals are applied controls direction as is known to the skilled artisan.

As will be appreciated, when the rotational drive mechanism in the handle 10 is actuated, either a turbine or electric motor or other rotational driver, and the drive shaft is spun or otherwise rotated at low unsustained speeds and/or unsustained rotational direction, the drive shaft 20 may experience resistance to rotation at the distal end of the drive shaft 20 and/or along its length. The torsional force within the drive shaft 20 may be lesser or greater depending on the amount of resistance experienced by the drive shaft 20 and the amount of rotational force imparted by the drive mechanism. In some cases, if the distal end encounters an obstruction and comes to an abrupt stop or experiences a quick acting resistance, the torsion in the shaft 20 may be affected by the rotational momentum of the drive shaft 20 and/or drive mechanism as well.

Figure 3:
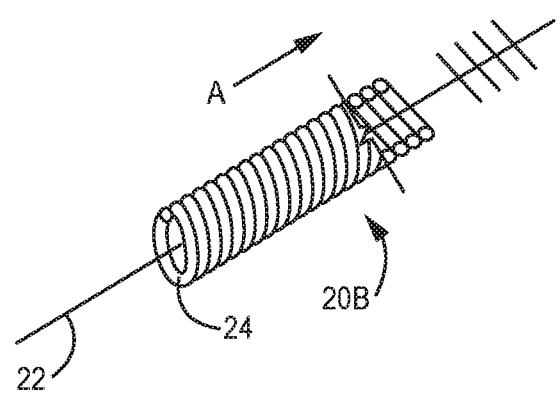
FIG. 3 illustrates one embodiment of the present invention.
Figure 4:
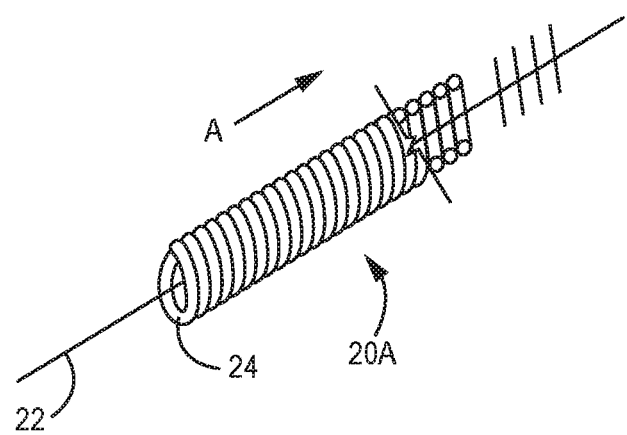
FIG. 4 illustrates one embodiment of the present invention.

It is to be appreciated that the direction that a drive shaft 20 is wound, compared to the direction it is driven, affects its response to being driven and, in particular, its response to startup and its response to encountering an obstruction. That is, the drive shaft 20 may include a coiled wire, or wire filars, that may be formed by winding on a mandrel, or otherwise formed. As shown in FIGS. 3 and 4, the drive shaft 20 may be wound in one of two directions about a longitudinal axis as the coil extends along the axis in a direction A. In particular, as illustrated by FIG. 3, the wire 24 may be wound or coiled counterclockwise about the axis 22. In contrast, as shown in FIG. 4, the wire 24 may be wound or coiled clockwise about the axis 22. Depending on the direction that the resulting drive shafts 20 are driven, the coiled wires or filars may define a spin-to-open drive shaft 20A or a spin-to-close drive shaft 20B. For purposes of discussion and simplicity, the present discussion generally assumes that the driven direction is a clockwise drive direction when viewing a device from a proximal, or driving or handle, end of the device. For purposes of FIGS. 3 and 4, the drive end is at the left of the figure and resistance may be present along the coil and at the right side of the figure. As such, referring again to FIG. 3, this type of drive shaft 20 may be termed a spin-to-close drive shaft. This is because as the drive shaft 20B spins in the clockwise direction, resistance to such spinning has a tendency to cause the coil to get tighter or close. In contrast, as shown in FIG. 4, this type of drive shaft 20 may be termed a spin-to-open drive shaft 20A. This is because as the drive shaft 20A spins in the clockwise direction, resistance to such spinning has a tendency to cause the coil to get looser or open.

As shown near the distal end of each example in FIGS. 3 and 4, a portion is shown in cross-section showing that the windings or filars have a pitch defined by how much the windings or filars lay over relative to a line perpendicular to the longitudinal axis 22. For purposes of discussion going forward, schematic drawing lines that cross the longitudinal axis that are tipped rearwardly or, close to perpendicular, as in FIG. 3, will be understood to reflect a spin-to-close drive shaft 20B and lines that cross the longitudinal axis that are tipped forwardly as in FIG. 4, will be understood to reflect a spin-to-open drive shaft 20A. However, it is to be appreciated that these definitions are with respect to a clockwise drive direction and it is understood that reversing the drive direction may change a spin-to-open drive shaft 20A to a spin-to-close drive shaft 20B and vice versa.

Referring now to the Figures, and contemplating the known difficulties and issues associated with spin-to-open 20A and spin-to-close 20B drive shafts, a slow rotation system is disclosed that may be rotated in either rotational direction by the rotational driver and, in certain embodiments, in a controlled non-sustained rotational mode. Thus, e.g., in a PWM controlled rotation, the rotational speed is controlled as is the rotational direction by pulse width modulation signals that are controlled by a microprocessor controller in operative communication with the rotational driver. Non-sustained rotational driver, e.g., turbine or motor, speed and direction of rotation may also be controlled with a controller comprising a control circuit that is triggered by logic signals from a microprocessor, wherein the controller is in operative communication with the rotational driver.

Figure 1A:
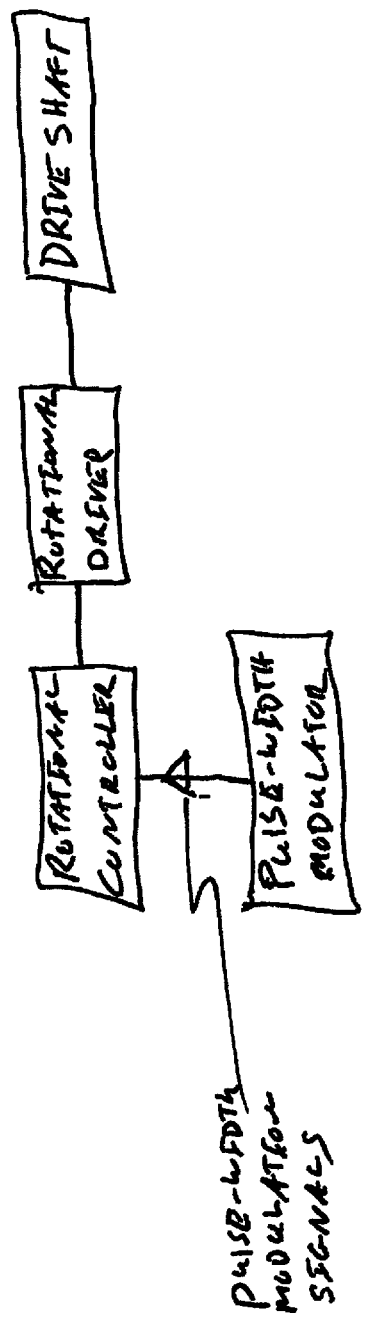
FIG. 1A illustrates one embodiment of the present invention.
Figure 2:
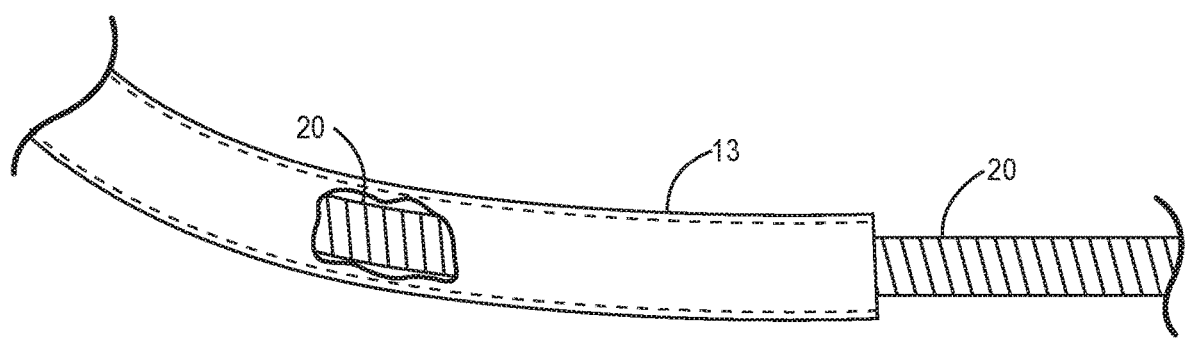
FIG. 2 illustrates one embodiment of the present invention.

One example of the PWM-controlled rotation is shown in FIG. 1A. Thus, the drive shaft is illustrated in operative connection with the rotational driver which is, in turn, in operative communication with the rotational controller which is in operative communication and connection with the pulse-width modulator. As shown, the pulse-width modulator generates and sends signals to the rotational controller for controlling the rotational direction of the drive shaft, via the rotational driver.

As defined herein, non-sustained speed is defined as controlled (by the rotational controller) speed that is not continuous or steady over the course of a procedure. Instead, the non-sustained speed moves from speed to speed as controlled by the rotational controller. In some embodiments, the devices and methods of the present invention may comprise non-sustained rotational direction wherein the rotational controller controls the non-continuous rotational direction during a procedure, alternating between a spin-to-open and a spin-to-close rotational direction. The controlled non-continuous rotational direction embodiments may be combined with the non-continuous rotational speed embodiments.

The controlled low rotational speed, non-sustained mode(s), i.e., rotational speed and/or rotational direction, are effective in eliminating friction between sliding components, and the resulting static friction buildup, during normal high-speed sustained rotational atherectomy. In addition, the controlled non-sustained and low rotational speed mode(s) proactively work to eliminate tissue wrapping or winding around the drive shaft 20 during a procedure.

As mentioned previously, an atherectomy device may include a handle portion 10 having an air-pressure driven turbine, an electric motor, or another type of drive mechanism for rotationally driving the drive shaft 20. The drive shaft 20 may extend distally from the handle 10 to a distal end where a crown 27 may be positioned. The crown 27 may be usable to clear arterial blockages and the like.

In one aspect, the drive shaft 20 may be rotated as a spin-to-open drive shaft at low, non-sustained, rotational speeds. In another aspect, the drive shaft 20 may be rotated as a spin-to-close drive shaft at low, non-sustained, rotational speeds.

In either case, the rotation may cause tissue to wind or wrap on or around the drive shaft 20 after rotating in a first direction. Reversing rotation of the drive shaft 20 in the second rotational direction is likely to cause the wound or wrapped tissue to unwind and/or unwrap from the drive shaft 20. Rotation in the first direction at low, non-sustained rotational speed may now resume. In this situation, the first rotational direction may be either spin-to-open or spin-to-close, while the second rotation is the opposite rotational direction of the first rotational direction.

Further, rotation of the drive shaft 20 at low, non-sustained, rotational speeds in a first rotational direction, either spin-to-open or spin-to-close, may result in a stall situation where the drive shaft distal tip becomes stuck in an occlusion or lesion. Reversing the rotational direction of the drive shaft 20 to the second rotational direction, opposite that of the first rotational direction, will assist the drive shaft 20 in unwinding from the occlusion or lesion.

Various embodiments of the present invention may be incorporated into a rotational atherectomy system as described generally in U.S. Pat. No. 6,494,890, entitled "ECCENTRIC ROTATIONAL ATHERECTOMY DEVICE," which is incorporated herein by reference. Additionally, the disclosure of the following co-owned patents or patent applications are herein incorporated by reference in their entireties: U.S. Pat. No. 6,295,712, entitled "ROTATIONAL ATHERECTOMY DEVICE"; U.S. Pat. No. 6,132,444, entitled "ECCENTRIC DRIVE SHAFT FOR ATHERECTOMY DEVICE AND METHOD FOR MANUFACTURE"; U.S. Pat. No. 6,638,288, entitled "ECCENTRIC DRIVE SHAFT FOR ATHERECTOMY DEVICE AND METHOD FOR MANUFACTURE"; U.S. Pat. No. 5,314,438, entitled "ABRASIVE DRIVE SHAFT DEVICE FOR ROTATIONAL ATHERECTOMY"; U.S. Pat. No. 6,217,595, entitled "ROTATIONAL ATHERECTOMY DEVICE"; U.S. Pat. No. 5,554,163, entitled "ATHERECTOMY DEVICE"; U.S. Pat. No. 7,507,245, entitled "ROTATIONAL ANGIOPLASTY DEVICE WITH ABRASIVE CROWN"; U.S. Pat. No. 6,129,734, entitled "ROTATIONAL ATHERECTOMY DEVICE WITH RADIALLY EXPANDABLE PRIME MOVER COUPLING"; U.S. Pat. No. 8,597,313, entitled "ECCENTRIC ABRADING HEAD FOR HIGH-SPEED ROTATIONAL ATHERECTOMY DEVICES"; U.S. Pat. No. 8,439,937, entitled "SYSTEM, APPARATUS AND METHOD FOR OPENING AN OCCLUDED LESION"; U.S. Pat. Pub. No. 2009/0299392, entitled "ECCENTRIC ABRADING ELEMENT FOR HIGH-SPEED ROTATIONAL ATHERECTOMY DEVICES"; U.S. Pat. Pub. No. 2010/0198239, entitled "MULTI-MATERIAL ABRADING HEAD FOR ATHERECTOMY DEVICES HAVING LATERALLY DISPLACED CENTER OF MASS"; U.S. Pat. Pub. No. 2010/0036402, entitled "ROTATIONAL ATHERECTOMY DEVICE WITH PRE-CURVED DRIVE SHAFT"; U.S. Pat. Pub. No. 2009/0299391, entitled "ECCENTRIC ABRADING AND CUTTING HEAD FOR HIGH-SPEED ROTATIONAL ATHERECTOMY DEVICES"; U.S. Pat. Pub. No. 2010/0100110, entitled "ECCENTRIC ABRADING AND CUTTING HEAD FOR HIGH-SPEED ROTATIONAL ATHERECTOMY DEVICES"; U.S. Design Pat. No. D610258, entitled "ROTATIONAL ATHERECTOMY ABRASIVE CROWN"; U.S. Design Pat. No. D6107102, entitled "ROTATIONAL ATHERECTOMY ABRASIVE CROWN"; U.S. Pat. Pub. No. 2009/0306689, entitled "BIDIRECTIONAL EXPANDABLE HEAD FOR ROTATIONAL ATHERECTOMY DEVICE"; U.S. Pat. Pub. No. 2010/0211088, entitled "ROTATIONAL ATHERECTOMY SEGMENTED ABRADING HEAD AND METHOD TO IMPROVE ABRADING EFFICIENCY"; U.S. Pat. Pub. No. 2013/0018398, entitled "ROTATIONAL ATHERECTOMY DEVICE WITH ELECTRIC MOTOR"; and U.S. Pat. No. 7,666,202, entitled "ORBITAL ATHERECTOMY DEVICE GUIDE WIRE DESIGN." It is contemplated by this invention that the features of one or more of the embodiments of the present invention may be combined with one or more features of the embodiments of atherectomy devices described therein.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method of performing rotational atherectomy with controlled alternating rotational directions, comprising:
   providing an atherectomy device with a rotational driver,
   providing a drive shaft comprising wire filars, the drive shaft in operative connection with the rotational driver, and
   providing a rotational controller in operative communication with the rotational driver,
   providing a pulse-width modulator (PWM) that is in operational communication with the rotational controller and with the rotational driver and adapted to receive signals from the rotational controller, the PWM further adapted to generate PWM signals based on the received signals from the rotational controller,
   wherein the generated PWM signals are sent to the rotational driver to control the rotational driver's rotational direction and rotational speed;
   inserting the drive shaft into a blood vessel;
   controlling, with the generated PWM signals, the rotational direction and rotational speed of the rotational driver and drive shaft to initiate rotating in a first rotational direction;
   controlling, with the generated PWM signals, the rotational direction and rotational speed of the rotational driver and drive shaft to initiate rotating in a second rotational direction; and
   after the rotating is initiated in the first and second rotational directions, with the generated PWM signals, alternating between controlling driving of the rotational driver and rotation of the drive shaft in the first rotational direction and controlling driving of the rotational driver and rotation of the drive shaft in the second rotational direction.

2. The method of claim 1, further comprising proactively controlling and eliminating tissue wrapping and/or tissue winding around the rotating drive shaft.

3. The method of claim 1, further comprising providing an abrasive element on the drive shaft.

4. The method of claim 1, wherein the rotational driver comprises an electric motor.

5. The method of claim 1, wherein the rotational speed is limited to less than 50,000 rpm.

6. The method of claim 1, wherein the rotational speed is limited to less than 25,000 rpm.

7. The method of claim 1, wherein the rotational speed is limited to less than 5,000 rpm.

8. The method of claim 1, further comprising the first rotational direction comprising a direction that unwinds the wound wire filars of the drive shaft and wherein the second rotational direction comprises a rotational direction that winds up the wire filars of the drive shaft.

9. The method of claim 8, wherein the drive shaft comprises a length when rotated in the first rotational direction and wherein the length of the drive shaft decreases when rotated in the second rotational direction.

10. The method of claim 8, wherein the drive shaft comprises a diameter when rotated in the first direction and wherein the diameter of the drive shaft increases when rotated in the second rotational direction.

11. The method of claim 1, further comprising the first rotational direction comprising a rotational direction that winds up the wound wire filars of the drive shaft and wherein the second rotational direction comprises a rotational direction that unwinds the wire filars of the drive shaft.

12. The method of claim 11, wherein the drive shaft comprises a length when rotated in the first rotational direction and wherein the length of the drive shaft increases when rotated in the second rotational direction.

13. The method of claim 11, wherein the drive shaft comprises a diameter when rotated in the first direction and wherein the diameter of the drive shaft decreases when rotated in the second rotational direction.

14. The method of claim 1, wherein the rotational speed of the rotational driver and drive shaft is controlled to a fixed or variable rotational speed.

\* \* \* \* \*